United States Patent [19]

Grau

[11] Patent Number: 4,639,332
[45] Date of Patent: Jan. 27, 1987

[54] PROCESS FOR THE PREPARATION OF INSULIN DERIVATIVES

[75] Inventor: Ulrich Grau, Hofheim am Taunus, Fed. Rep. of Germany

[73] Assignee: Hoechst Aktiengesellschaft, Fed. Rep. of Germany

[21] Appl. No.: 636,672

[22] Filed: Aug. 1, 1984

[30] Foreign Application Priority Data

Aug. 3, 1983 [DE] Fed. Rep. of Germany ....... 3327928

[51] Int. Cl.$^4$ ............................................. C07K 7/40
[52] U.S. Cl. .................................................. 530/303
[58] Field of Search ...................................... 260/112.7

[56] References Cited

U.S. PATENT DOCUMENTS 2,920,014  1/1960  Petersen et al. ................... 260/112.7
3,884,897  5/1975  Geiger et al. ...................... 260/112.7

OTHER PUBLICATIONS

*Chemical Abstracts*, vol. 79, (1973), 76289c.

*Primary Examiner*—Frederick E. Waddell
*Attorney, Agent, or Firm*—Finnegan, Henderson, Farabow, Garrett & Dunner

[57] ABSTRACT

The invention relates to a process for the preparation of insulin derivatives of the formula I

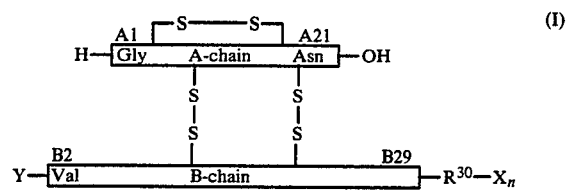

in which $R^{30}$ represents the radical of a neutral L-amino acid which can be genetically coded, X represents identical or different radicals of L-amino acids which can be genetically coded, at least one of which is a basic amino acid, it being possible for the C-terminal member to be homoserine-lactone, Y denotes Phe or H and n denotes 1, 2 or 3, by splitting of intermediates, proinsulin, preproinsulin or analogs thereof, which comprises carrying out the splitting reaction close to the isoelectric point of the insulin derivatives of the formula I in the presence of an aromatic hydroxy compound.

10 Claims, No Drawings

PROCESS FOR THE PREPARATION OF INSULIN DERIVATIVES

Insulin is synthesized in vivo in the form of a precursor called preproinsulin. The presequence represents a signal region for interactions with membranes and is split off during or immediately after the synthesis. In contrast, proinsulin is a molecule which can be detected in small amounts in pancreas extracts. During its conversion to insulin, the C-peptide is split off by a specific enzyme system.

The cutting sites for the processing enzymes are formed by the sequences Arg-Arg at positions B31 and B32 (B30 is later the C-terminal of the B chain) and Lys-Arg at position 62 (or A 1) and 63 (or A0), which are N-terminal to the later A-chain. Proinsulin can be converted smoothly into insulin in vitro with enzymes having tryptic and carboxypeptidase B activity (Kemmler et al., JBC 246, 6786–91 (1971)). In contrast, proteolysis with trypsin or trypsin-like enzymes alone preferentially gives those intermediates which still carry one or both arginines in positions 31 and 32 on the C-terminal of the B chain, besides those insulin degradation products which are split B-terminally to give lysine-(B29)-insulin (=dealanine-(B30)-porcine insulin, de-threonine-(B30)-human insulin) or to give arginine-(B22)-insulin (=deoctapeptide insulin) (Chance, in Proc. VII Congress of International Diabetes Fed., (1970); D.E. Steiner et al., Fed. Proc. 33, 2105–15 (1974); J. Markussen in Proc. Symp. on Proinsulin, Insulin, C-Peptide, Tokushima (1978)).

Preproinsulins are at present accessible by genetic engineering methods from prokaryotes, in particular E. coli. Those strains which contain proinsulins with a human insulin sequence are of particular interest here. Moreover, by modification of the plasmids it is possible to construct new sequence sections in a controlled manner, in particular by changes in positions 31-33 and 61-63 of the proinsulin sequence in a manner such that enzymatic or chemical cleavage sites are retained for the release of insulin or insulin derivatives. These include, for example, those derivatives which contain, instead of one or both arginines at positions 31 and 32, another basic amino acid, i.e. lysine or histidine, so that enzymes having a tryptic specificity can be used for the cleavage. However, it is also possible to introduce sequences which are substrates of other known proteolytic enzymes, or sequences on which cleavage by chemical methods is possible. The precondition for the present invention is only that, on suitable cleavage of the proinsulin analog, an insulin derivative is formed which contains no additional amino acid before the N-terminal of the A chain and carries at least one basic amino acid amongst the up to three additional amino acids on the C-terminal of the B chain (positions 31-33).

Those insulin derivatives which additionally have positive charges on the C-terminal of the B chain, processes for their preparation, agents containing them and their use are the subject of U.S. patent application Ser. Nos. 632.845 and 632,859. A process for their crystallization is the subject of U.S. patent application Ser. No. 635,257.

It has now been found that these insulin derivatives can be prepared particularly smoothly from the corresponding intermediates, proinsulins, preproinsulins or the corresponding analogs by carrying out the proteolytic digestion or the chemical splitting close to the isoelectric point of the desired derivative in the presence of phenol or similar aromatics. By this means, not only is the end product precipitated from the reaction solution and thus substantially withdrawn from the reaction equilibrium; but also sharp-edged, prism-shaped crystals which, because of their low surface area, are far less liable to undergo further reaction than, for example, amorphous precipitates, are formed directly in the medium under the conditions described. Thus, for example, it is surprising that the derivative insulin-$Arg^{B31}$-OH in crystalline form is exceptionally stable to further tryptic degradation.

The invention thus relates to a process for the preparation of insulin derivatives of the formula I

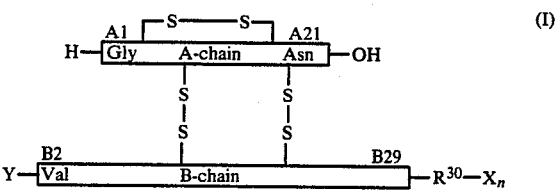

in which
 $R^{30}$ represents the radical of a neutral L-amino acid which can be genetically coded,
 X represents identical or different radicals of L-amino acids which can be genetically coded, at least one of which is a basic amino acid, it being possible for the C-terminal member to be the homoserine-lactone radical,
 Y = Phe or H and
 n = 1, 2 or 3, by splitting of intermediates, proinsulin, preproinsulin or analogs thereof, which comprises carrying out the splitting reaction close to the isoelectric point of the insulin derivatives of the formula I in the presence of an aromatic hydroxy compound.

Y is preferably Phe.

The following L-amino acids can be genetically coded: Gly, Ala, Ser, Thr, Val, Leu, Ile, Asp, Asn, Glu, Gln, Cys, Met, Arg, Lys, His, Tyr, Phe, Trp and Pro (neutral amino acids underlined).

A neutral amino acid is understood as meaning, in particular, Gly, Ala, Ser, Thr, Val, Leu, Ile, Asn, Gln, Met, Phe or Pro; a basic amino acid is understood as meaning, in particular, Arg, Lys or His.

The following insulin derivatives, for example, can be prepared by the process according to the invention (without the invention being restricted to these):

Human insulin—$Arg^{B31}$—OH

Porcine insulin—$Arg^{B31}$—OH

Bovine insulin—$Arg^{B31}$—OH

Human insulin—$Arg^{B31}$—$Arg^{B32}$—OH

Porcine insulin—$Arg^{B31}$—$Arg^{B32}$—OH

Bovine insulin—$Arg^{B31}$—$Arg^{B32}$—OH

Human insulin—$Lys^{B31}$—OH

Human insulin—$Ala^{B31}$—$Lys^{B32}$—OH

Human insulin—$Val^{B31}$—$Arg^{B32}$—OH

Human insulin—$Leu^{B31}$—$Arg^{B32}$—$Arg^{B33}$—OH

Porcine insulin—Val$^{B31}$—His$^{B32}$—Arg$^{B33}$—OH

Porcine insulin—Leu$^{B31}$—Val$^{B32}$—Arg$^{B33}$—OH

Human insulin—Arg$^{B31}$—Phe$^{B32}$—OH

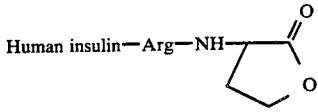

The process according to the invention is preferably carried out in a pH range from one pH unit below the isoelectric point to one unit above this point in the presence of a phenol or of a mixture of several phenols.

The pH can be set up by suitable buffers (such as acetates, citrate or phosphate).

In the process according to the invention, the reaction is preferably carried out such that the concentration of starting material is 0.5–30 mg/ml, preferably 1–10 mg/ml, and the rate of reaction is slightly greater than or equal to the rate of formation of the crystals. This means that many crystal seeds are formed and the crystal size thus does not exceed 30 μm on average. It is possible, particularly in the case of enzyme catalysis, to control the rate of reaction very accurately in the desired manner.

With the process described, better steering of the reaction in the direction of the desired product and hence a significant improvement in the yield are thus possible. The product is obtained in a form which can easily be further processed and which can be substantially freed from excess splitting reagent, for example proteases, by simply washing.

The splitting reagent chosen is, for example, a protease with a specificity such that the desired radical $X_n$ is retained, whilst the A chain has a free N-terminal H-Gly after splitting has been carried out. If methionines are introduced at the corresponding sites in the proinsulin sequence, splitting can be carried out with cyanogen bromide, in which case the homoserine-lactone radical is retained on the C-terminal.

Insulin derivatives of the formula I and pharmaceutical agents containing these are completely novel delayed action principles in which the action can be brought about without depot auxiliaries, such as zinc or protamine sulfate. The depot action is attributed to an inherent physical principle resulting from protein chemistry, that is to say the sparing solubility of the insulin derivative at the isoelectric point. Redissolving thereof under physiological conditions is possibly achieved by splitting off the additional basic groups, which, depending on the derivative, takes place by tryptic or trypsin-like and/or carboxypeptidase B or carboxypeptidase B-like and/or esterase activity.

EXAMPLE 1

Tryptic digestion of denonapeptide-proinsulin from pigs in the absence and in the presence of a phenol.

350 mg of denonapeptide-porcine proinsulin were dissolved under acid conditions and the solution was added to 215 ml of 0.1M tris buffer, pH=7.5, containing 200 μg of trypsin (bovine). Turbidity occurred within a few minutes. When the reaction had ended (about 1 hour), 100 μg of trypsin inhibitor were added, the mixture was centrifuged and the white precipitate was dissolved in 20 ml of 0.05M ammonium acetate buffer, pH=4.0, with 0.1% of a suitable detergent and purified on a cation exchanger with a 0 to 1M sodium chloride gradient. The following were isolated: 96 mg (36.6% of insulin-Arg$^{B31}$-Arg$^{B32}$-OH, in the pure form, and 72 mg (27.4%) of a mixture of insulin-Arg$^{B31}$-Arg$^{B32}$-OH and insulin-Arg$^{B31}$-OH and at least two further impurities (according to isoelectric focussing and high pressure liquid chromatography (HPLC)). 56 mg (about 21%) of a mixture containing 14.9% of starting substance, 8.7% of di- and mono-arginine derivative, 49.3% of de-alanine(B30)-insulin and 12.2% of deoctapeptide-insulin, in addition to a few smaller, unidentified peaks (HPLC), were isolated from the supernatant of the reaction.

In a parallel batch, 100 mg of denonapeptide-porcine proinsulin were dissolved under acid conditions and the solution was added to 50 ml of a 0.1M tris buffer, pH=7.5, containing 2.5 mg/ml of m-cresol and 50 μg of trypsin (bovine). After about 15 minutes, a crystalline precipitate of sharp-edged prisms about 5–15 μm in size formed. The reaction was interrupted in the manner described after 3 hours. Working up was carried out as described above.

Yield: 56 mg (74.7%) of insulin-Arg$^{B31}$-Arg$^{B32}$-OH; 11 mg (14.7%) of a mixture of di-arginine and mono-arginine derivative.

Only a trace of insulin-like substances remained in the supernatant.

EXAMPLE 2

Preparation of human insulin-Arg$^{B31}$-OH from monkey preproinsulin, expressed in E. coli, by tryptic digestion.

10 mg of monkey preproinsulin are dissolved under acid conditions and the solution is added to 5 ml of 0.1M phosphate buffer with 0.5M of sodium chloride, pH=6.8, containing 1.5 mg/ml of phenol and 0.7 mg/ml of m-cresol, as well as 25 μg of trypsin (bovine). The desired product precipitates out of the reaction solution in sharp-edged prisms about 5–20 μm in size. The crystals contain 92% of insulin and insulin derivatives; according to HPLC, 78% of the product is human insulin-Arg$^{B31}$-OH and 14% is human insulin-Arg$^{B31}$-Arg$^{B32}$-OH. Only less than 5% of insulin-like protein is found in the clear supernatant of the reaction. If the crystal suspension is left to stand in the presence of trypsin at room temperature for a further 2 days, 87% of the theoretical amount of insulin and insulin derivatives are still in the crystalline state, 79% of the product being human insulin-Arg$^{B31}$-OH and 11% being human insulin-Arg$^{B31}$-Arg$^{B32}$-OH.

I claim:

1. A process for the preparation of an insulin derivative of the formula I

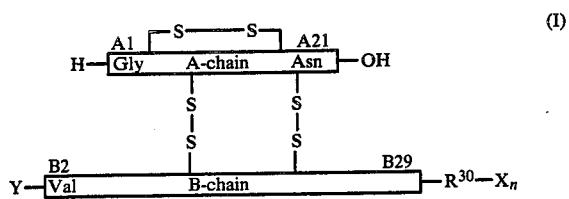

in which $R^{30}$ represents the radical of a neutral L-amino acid selected from the group consisting of Ala, Thr, and Ser, n=1, 2 or 3, X represents identical or different radicals of naturally occurring L-amino acids which can be genetically coded, at least one of which is a basic amino acid, and, where n is 2 or 3, the C-terminal member may also be homoserine-lactone, Y=Phe or H by splitting of proinsulin intermediates, proinsulin, preproinsulin or analogs thereof, which comprises carrying out the splitting reaction at a pH in the range from 1 pH unit below the isoelectric point of each individual insulin derivative of the formula I to 1 pH unit above said isoelectric point in the presence of at least one phenol.

2. The process as claimed in claim 1, wherein at least one of X in formula I represents Lys or Arg.

3. The process as claimed in claim 1, wherein the reaction product is obtained in the form of crystals up to 30 μm in size.

4. The process as claimed in claim 1, wherein Y in formula I represents Phe.

5. The process as claimed in claim 1, wherein the insulin derivative of the formula I has the sequence of human insulin, porcine insulin or bovine insulin.

6. The process as claimed in claim 1, wherein the proinsulin intermediate, the proinsulin or the analog thereof is present in the reaction medium in a concentration of 0.5 to 30 mg/ml at the start of the reaction.

7. The process as claimed in claim 1, wherein the reaction medium is an aqueous medium buffered in a suitable manner.

8. The process as claimed in claim 1, wherein the splitting reagent is a protease, the specificity of which is such that the desired radical $X_n$ is retained, whilst the A chain has a free N-terminal after splitting has been carried out.

9. The process as claimed in claim 1, wherein the splitting reagent is cyanogen bromide, the homoserine-lactone radical being retained on the C-terminal of the B chain, while the natural N-terminal of the A chain is formed on splitting at Met-A0.

10. The process as claimed in claim 6, wherein the concentration is in the range from 1 to 10 mg/ml.

* * * * *